United States Patent
Qian et al.

(10) Patent No.: US 11,594,152 B2
(45) Date of Patent: Feb. 28, 2023

(54) LINK MOTION-BASED FOOD SWALLOWING SIMULATOR

(71) Applicant: Jiangnan University, Wuxi (CN)

(72) Inventors: Shanhua Qian, Wuxi (CN); Wenshu Feng, Wuxi (CN); Yue Wu, Wuxi (CN); Jinghu Yu, Wuxi (CN); Zifeng Ni, Wuxi (CN)

(73) Assignee: Jiangnan University, Wuxi (CN)

( * ) Notice: Subject to any disclaimer, the term of this patent is extended or adjusted under 35 U.S.C. 154(b) by 517 days.

(21) Appl. No.: 16/754,376

(22) PCT Filed: Aug. 2, 2018

(86) PCT No.: PCT/CN2018/098214
§ 371 (c)(1),
(2) Date: Apr. 8, 2020

(87) PCT Pub. No.: WO2019/237471
PCT Pub. Date: Dec. 19, 2019

(65) Prior Publication Data
US 2020/0242975 A1   Jul. 30, 2020

(30) Foreign Application Priority Data
Jun. 11, 2018 (CN) .......................... 201810594464.8

(51) Int. Cl.
*G09B 23/32* (2006.01)
*A61B 5/00* (2006.01)

(52) U.S. Cl.
CPC ............ *G09B 23/32* (2013.01); *A61B 5/4205* (2013.01)

(58) Field of Classification Search
CPC ...... G09B 23/28; G09B 23/30; G09B 23/303; G09B 23/32

(Continued)

(56) References Cited

U.S. PATENT DOCUMENTS 5,525,305 A * 6/1996 Minekus ................. B01F 31/55
422/111
5,993,406 A * 11/1999 Rozga .................... G09B 23/28
604/6.09

(Continued)

FOREIGN PATENT DOCUMENTS

CN         206140506 U  *  5/2017  ................ B25J 9/10
CN         107154208 A  *  12/2017 ............. G09B 23/28

*Primary Examiner* — Kurt Fernstrom
(74) *Attorney, Agent, or Firm* — Idea Intellectual Limited; Margaret A. Burke; Sam T. Yip

(57) ABSTRACT

The present invention discloses a link motion-based food swallowing simulator comprising a swallowing module including a bionic oral cavity assembly, a shred collecting assembly and a supporting assembly wherein two side plates of a maxillary base of the bionic oral cavity assembly connect to a mounting plate of the supporting assembly, wherein the shred collecting assembly is positioned on a mounting base of the supporting assembly; an adjusting module, positioned under the mounting base, includes a bearing assembly and an adjusting assembly wherein the bearing assembly is disposed on the adjusting assembly, achieving the simulation of the food swallowing mechanism from static to dynamic. The adoption of the driving module realizes the swallowing action through link motion simulation, simulating the swallowing process of the human body and the swallowing process of the patient lying on the back through adjusting modules, improving the swallowing situation with higher adaptability.

10 Claims, 3 Drawing Sheets

(58) Field of Classification Search
USPC .......................................................... 434/127
See application file for complete search history.

(56) References Cited

U.S. PATENT DOCUMENTS

| | | | | |
|---|---|---|---|---|
| 6,022,733 | A * | 2/2000 | Tam | ........................ C12M 29/16 |
| | | | | 435/298.2 |
| 8,092,222 | B2 * | 1/2012 | Wickham | .............. B01F 33/821 |
| | | | | 434/127 |
| 8,257,085 | B2 * | 9/2012 | Alric | ........................ G09B 23/32 |
| | | | | 434/272 |
| 9,575,044 | B2 * | 2/2017 | Minekus | ................. G09B 23/32 |
| 10,127,839 | B2 * | 11/2018 | Legen | .................. G09B 23/303 |

* cited by examiner

LINK MOTION-BASED FOOD SWALLOWING SIMULATOR

CROSS-REFERENCE TO RELATED APPLICATION

This application is a 371 application of the International Patent Application No. PCT/CN2018/098214 filed on Aug. 2, 2018, which claims priority from the Chinese invention patent application no. 2018105944648 filed on Jun. 11, 2018, and the disclosures of which are incorporated herein by reference in their entireties.

FIELD OF THE INVENTION

The present invention relates to the technical field of oral bionic mechanical technology. More particularly, it relates to a link motion-based food swallowing simulator.

BACKGROUND OF THE INVENTION

With the growth of aging population and the gradually deteriorating swallowing function of the elderly, dysphagia becomes more common in the society. However, due to the complexity of the structure and nervous system of the human swallowing system, it is difficult to obtain the in vivo measurement data of food flow in the swallowing system, which directly leads to the failure of applying medicine according to the indications, and hinders the research on the influence of the material characteristics of food to the swallowing process and the development of safe food. In order to improve the medical diagnostic level of dysphagia, a link motion-based food swallowing simulator is proposed, which can provide an in vitro test environment to study the flow characteristics of food when it is swallowed, which is of great significance for the research and treatment of dysphagia, so as to improve the quality of life of patients with dysphagia.

Most of the current structural models of swallowing system are static structural models, which is not able to demonstrate the swallowing process dynamically. Some of the dynamic structural models are relatively simple in structure and cannot correctly express the food swallowing process. Through the link motion mechanism, the swallowing simulator according to the present invention is able to simulate the curves of movement of the tongue, and further provides multiangle swallowing simulation with a variable inclination angle device, a collection box and a collection tank. The variable inclination angle device can well simulate the real swallowing status of people as their heads may move while swallowing. Therefore, the simulator is of great significance for the study of the real swallowing status in human body.

SUMMARY OF THE INVENTION

This section aims to summarize some aspects of the embodiments of the present invention and to briefly describe some preferred embodiments. The simplification or omission may be made in this section, the abstract of the specification, and the title to avoid obscuring the purpose of this section, the abstract of the specification, and the title. Such simplification or omission may not be used to limit the scope of the present invention.

The present invention is provided in view of the above-mentioned drawbacks of existing food swallowing simulator.

Therefore, the objective of the invention is to provide a link motion-based food swallowing simulator, which can achieve simulation of food swallowing mechanism from static to dynamic. The adoption of a driving module can realize the swallowing action through link motion simulation, which authentically simulate the swallowing process of the human body and simulate the swallowing process of the patient lying on the back through adjusting modules in the device, further improving the swallowing situation with higher adaptability. Meanwhile, additional sensors in a bionic oral cavity assembly can provide effective data for the relevant food and medical industry.

To solve the above technical problem, the present invention provides a link motion-based food swallowing simulator, comprising a swallowing module including a bionic oral cavity assembly, a shred collecting assembly, and a supporting assembly, wherein two side plates of a maxillary base of the bionic oral cavity assembly connect to a mounting plate of the supporting assembly, wherein the shred collecting assembly is positioned on a mounting base of the supporting assembly; a driving module, positioned in a mounting chamber (N1) of the mounting base; an adjusting module, positioned under the mounting base, including a bearing assembly and an adjusting assembly, wherein the bearing assembly is disposed on the adjusting assembly; and a base, including a protective housing and a base plate, wherein the protective housing is positioned on the base plate, and the protective housing is positioned on a periphery of the adjusting assembly.

In a preferred embodiment of the link motion-based food swallowing simulator according to the present invention, the bionic oral cavity assembly further comprises a tongue base, wherein the tongue base is positioned on an inner side of the maxillary base.

In a preferred embodiment of the link motion-based food swallowing simulator according to the present invention, an inner side of the maxillary base is equipped with a sensor.

In a preferred embodiment of the link motion-based food swallowing simulator according to the present invention, the tongue base includes a tongue-shaped soft pad and a support member, wherein the tongue-shaped soft pad is mounted on the support member.

In a preferred embodiment of the link motion-based food swallowing simulator according to the present invention, the shred collecting assembly includes a first collection box, a second collection box, a bottom slide, and a guiding slit, and wherein the first collection box is positioned at one end of a tongue tip of the tongue-shaped soft pad, the bottom slide is positioned between the second collection box and a base of the tongue-shaped soft pad, and the guiding slit is positioned at two sides of the tongue base.

In a preferred embodiment of the link motion-based food swallowing simulator according to the present invention, the driving module includes a driving unit, and one end of a first connecting rod of the driving unit is connected with a support member;

wherein, the driving unit further comprises a second connecting rod and a connecting rod base, and two ends of the second connecting rod are respectively hinged with the other end of the first connecting rod and a notch of the connecting rod base.

In a preferred embodiment of the link motion-based food swallowing simulator according to the present invention, the driving unit further comprises a stabilizing shaft and a bearing seat, one end of the stabilizing shaft passes through the first connecting rod, and the other end is mounted on the bearing seat, wherein the bearing seat is fastened on the mounting plate.

In a preferred embodiment of the link motion-based food swallowing simulator according to the present invention, wherein the driving module further comprises a power unit and a position limiting unit, wherein a lead screw of the driving unit is connected with a support side bearing seat through a fixed side bearing sear of the position limiting unit, and the lead screw is connected with an internal thread hole of a connecting rod base by screwing;

wherein the power unit further comprises a motor, and the motor passes through a fixing plate of the mounting base and is connected with the lead screw via a coupler.

In a preferred embodiment of the link motion-based food swallowing simulator according to the present invention, the bearing assembly includes a supporting frame and a rotating seat, wherein one end of the supporting frame is hinged with the rotating seat.

In a preferred embodiment of the link motion-based food swallowing simulator according to the present invention, the adjusting assembly includes a primary adjusting unit and an auxiliary adjusting unit, wherein a third connecting rod of the primary adjusting assembly is connected with a frame of a supporting frame, and wherein a first fixing seat of the auxiliary adjusting unit is connected with a lower partition of the mounting base.

wherein the primary adjusting unit further comprises a fourth connecting rod, a slide groove, a lever and a linear actuator, wherein a push lever of the linear actuator is connected with the lever, and the linear actuator is fastened to the protective housing of the base through a bolt, wherein a sliding block is positioned in two ends of the lever, and the sliding block is embedded in a slide groove, wherein two ends of the fourth connecting rod are respectively connected with the lever and the third connecting rod;

wherein the auxiliary adjusting unit further comprises a gas spring and a second fixing seat, wherein two ends of the gas spring are respectively connected with the first fixing seat and the second fixing seat.

The benefits of the present invention: the present invention is a reasonable and scientific design, simple structure, convenient to operate, and able to realize the simulation of the food swallowing mechanism from static to dynamic. The adoption of the driving module can realize the swallowing action through link motion simulation, which authentically simulate the swallowing process of the human body and simulate the swallowing process of the patient lying on the back through adjusting modules in the device, further improve the swallowing situation with higher adaptability. Meanwhile, the additional sensors in the bionic oral cavity assembly can provide effective data for the relevant food and medical industry.

BRIEF DESCRIPTION OF THE DRAWINGS

In order to explain the technical solution of the embodiment of the present invention more clearly, the drawings used in the description of the embodiments are briefly introduced below. Obviously, the drawings in the following description are only some embodiments of the present invention. Those of ordinary skill in the art may conceive other drawings according to these drawings without paying creative effort, wherein.

DETAILED DESCRIPTION

In order to make the foregoing objectives, features, and advantages of the present invention more comprehensible, specific embodiments of the present invention will be described in detail below with reference to the accompanying drawings.

In the following description, many specific details are set forth for fully understanding of the present invention, but the present invention can also be implemented in other ways different from those described here, and those skilled in the art can make similar applications without departing from the scope of the present invention, Therefore the present invention should not be limited by the specific embodiments disclosed below.

Furthermore, "an embodiment" or "embodiments" referred to herein refers to a particular feature, structure, or characteristic that can be included in at least one implementation of the present invention. The appearances of "one embodiment" in different places in this specification may not all refer to the same embodiment, nor are they separate or selective embodiments mutually exclusive with other embodiments.

Furthermore, the present invention is described in detail with reference to schematic diagrams. In the detailed description of the embodiments of the present invention, for convenience of explanation, cross-sectional views showing the structure of the device may be partially enlarged with specific proportions, and the schematic diagrams are merely examples, which should not be used here to limit the scope of protection of the present invention. In addition, the actual production of drawings should include three-dimensional dimensions of length, width and depth.

Figure 1:
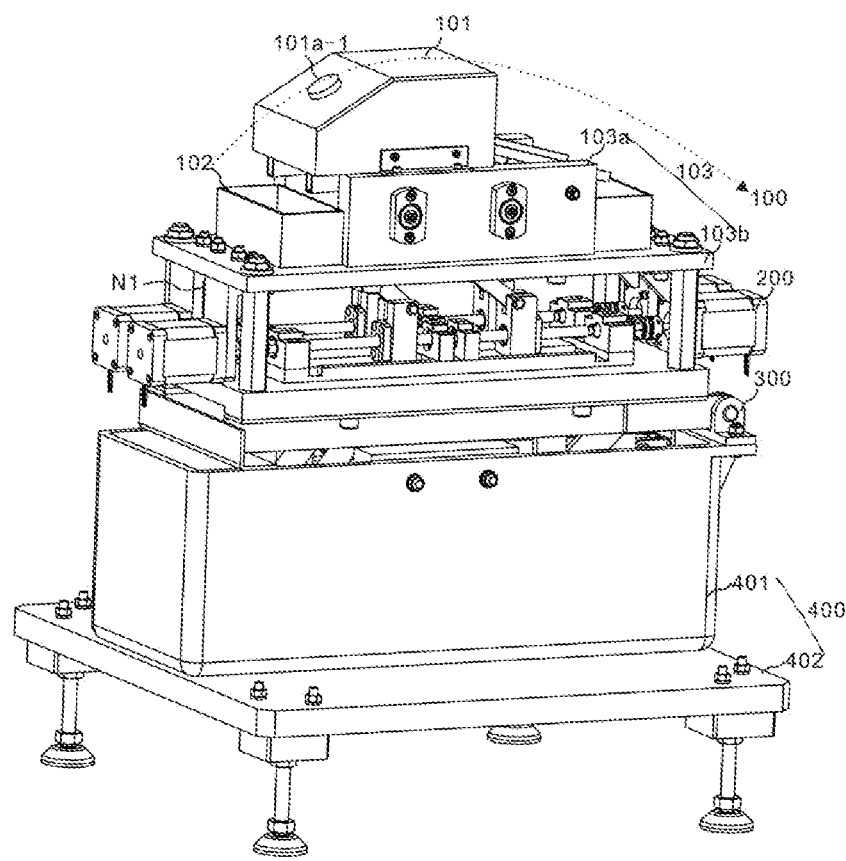
FIG. 1 is the overall structural diagram of a link motion-based food swallowing simulator according to the first embodiment of the present invention.
Figure 2:
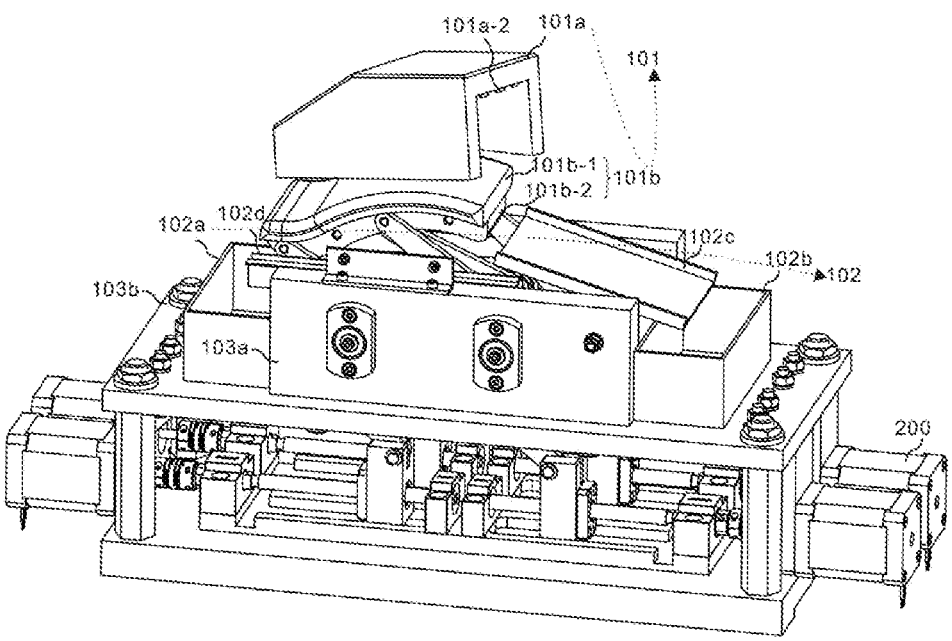
FIG. 2 is the local structural diagram of the link motion-based food swallowing simulator according to the first embodiment of the present invention.

Referring to FIGS. 1 and 2, according to a first embodiment of the present invention an overall structure diagram of a food swallowing simulator based on link motion is provided. As shown in FIG. 1, the link motion-based food swallowing simulator includes a swallowing module 100 including a bionic oral cavity assembly 101, a shred collecting assembly 102, and a supporting assembly 103, wherein two side plates of a maxillary base 101a of the bionic oral cavity assembly 101 connect to a mounting plates 103a of the supporting assembly 103, and the shred collecting assembly 102 is positioned on a mounting base 103b; a driving module 200 is disposed on a mounting chamber N1 of the mounting base 103b; an adjusting module 300 including a bearing assembly 301 and a adjusting assembly 302 is positioned under the mounting base 103b, wherein the bearing assembly 301 is disposed on the adjusting assembly 302; the base 400 is positioned on the bottom of the adjusting assembly 302.

More specifically, the main structure of the present invention includes the swallowing module 100, the driving module 200, the adjusting module 300 and the base 400. The four modules cooperate with each other to authentically simulate the swallowing process and realize simulation of the food swallowing mechanism from static to dynamic. The swallowing module 100 mimics the human oral cavity which collects the swallowing food and supports the driving module 200 and it includes the bionic oral cavity assembly 101, the shred collecting assembly 102, and the supporting assembly 103. The two side plates of the maxillary base 101a of the bionic oral cavity assembly 101 connect to the mounting plates 103a of the supporting assembly 103 through L-shaped mounting plates, and the two end faces of the L-shaped mounting plates fasten to the mounting plates 103a and the maxillary base 101a by bolt or fastener. The L-shaped mounting plate is made of stainless steel or plastic and a feeding port 101a-1 is disposed on the maxillary base 101a, wherein the maxillary base 101a includes a shell and an inner wall cavity surrounded by the shell and the inner cell wall mimics the human maxillary wall. Furthermore, the shell is made of plastic, and the inner cell wall is made of soft material or rubber. The shred collecting assembly 102 is arranged on the upper partition of the mounting base 103b of the supporting assembly 103 and the shred collecting assembly 102 and the upper partition of the mounting base 103b are not fixed so as to allow cleaning up food shreds in the shred collecting assembly 102. Preferably, the shred collecting assembly 102 is made of plastic material. It should be noted that the inner wall of the maxillary base 101a is also equipped with a sensor 101a-2, wherein the sensor 101a-2 is configured to measure the pressure applied to the food during the swallowing process. Comparing to the results of the normal swallowing, the relative movement between the maxillary base 101a and a tongue base 101b can provide relative data for relevant food and medical industries. Preferably, the sensor 101a-2 is a micro force sensor or pressure sensor, etc.; and the driving module 200 embedded in the mounting chamber N1 between the upper partition and lower partition of the mounting base 103b is a power mechanism to achieve the human swallowing simulation; the adjusting module 300 positioned under the mounting base 103b can simulate the food swallowing process with multi angle and enhance the practical performance of the present invention. Furthermore, the adjusting module 300 includes a bearing assembly 301 and adjusting assembly 302, wherein the bearing assembly 301 positioned on the adjusting assembly 302 is configured to carry the swallowing module 100 and driving module 200, and the adjusting assembly 302 is configured to perform adjusting function. The base 400 includes a protective housing 401 and a base plate 402, wherein the protective housing 401 is positioned on the base plate 402 and both of them are integral construction. The protective housing 401 is positioned on the periphery of the adjusting assembly 302.

Wherein, the bionic oral cavity assembly 101 also includes the tongue base 101b, wherein the tongue base 101b is positioned on the inner side of the maxillary base 101a, and both of them constitute a human oral cavity. When in use, the tongue base 101b can touch the inner wall of the maxillary base 101a so as to simulate the food swallowing process. Furthermore, the tongue base 101b includes a tongue-shaped soft pad 101b-1 and a support member 101b-2, wherein the tongue-shaped soft pad 101b-1 is mounted on the support member 101b-2. Preferably, the tongue-shaped soft pad 101b-1 and the support member 101b-2 are formed in one integral structure, and made of PDMS.

The shred collecting assembly 102 includes a first collection box 102a, a second collection box 102b, a bottom slide 102c, and a guiding slit 102d, wherein the first collection box 102a is positioned at one end of a tongue tip of the tongue-shaped soft pad 101b-1, the guiding slit 102d is positioned around two sides of the tongue base 101b, and one end of the guiding slit 102d is disposed on the first collection box 102a, cooperating with each other so as to collect small amount of food leaked from both sides of the tongue into the guiding slit 102d. The bottom slide 102c is positioned between the second collection box 102b and the base of the tongue-shaped soft pad 101b-1 so as to guide the food. Preferably, one end of the bottom slide 102c is connected to the base of the tongue-shaped soft pad 101b-1, and the other end is positioned on the opening of the second collection box 102b such that no matter how the tongue base 101b move, food would be collected to ensure the use thereof being convenient and practical.

Figure 3:
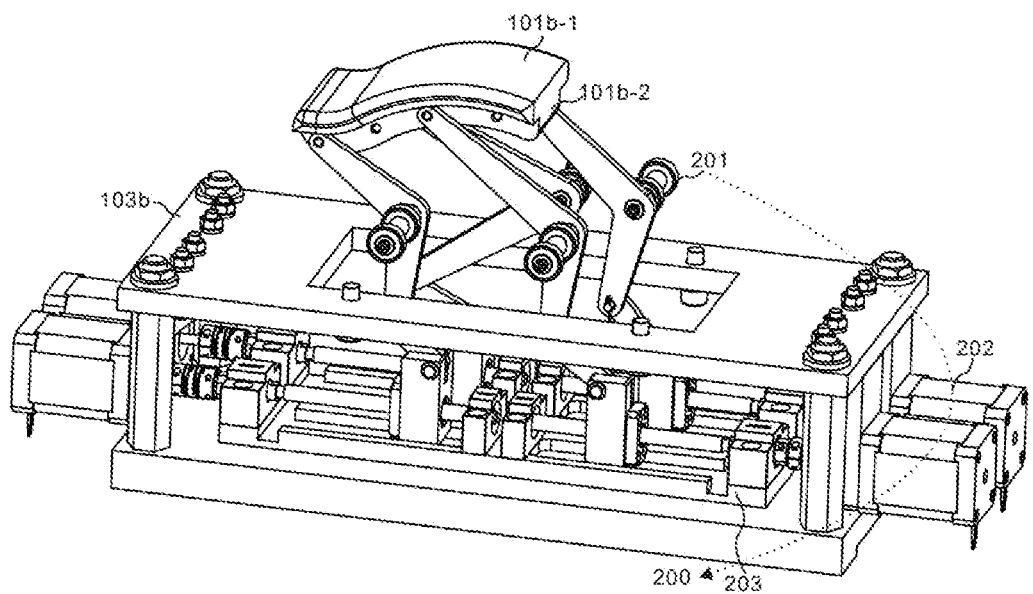
FIG. 3 is a local structural schematic diagram of the first perspective view of a link motion-based food swallowing simulator according to the second embodiment of the present invention.
Figure 4:
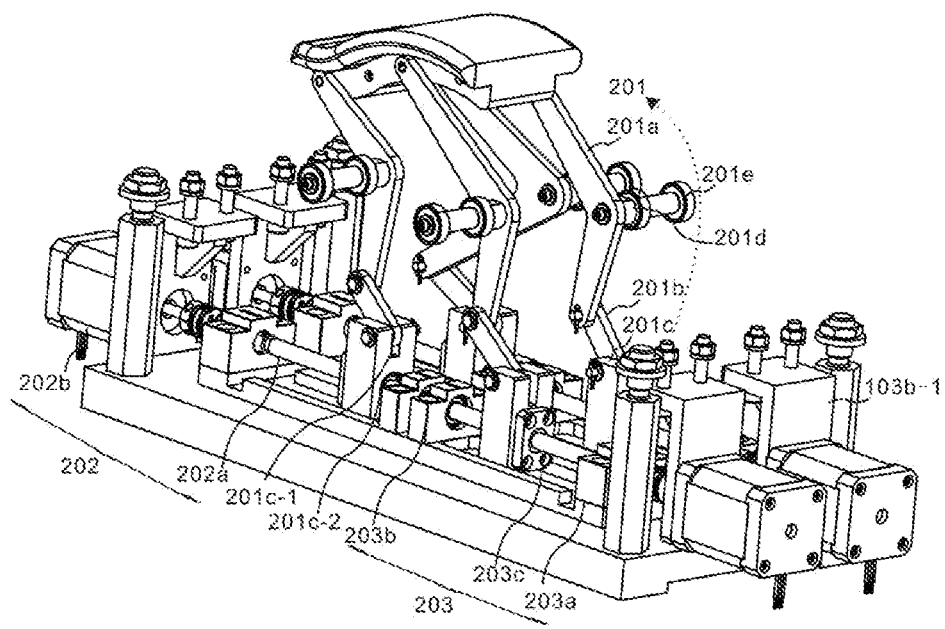
FIG. 4 is a local structural schematic diagram of the second perspective view of the link motion-based food swallowing simulator according to the second embodiment of the present invention.

Referring to FIGS. 3 and 4, it is the second embodiment of the present invention, which is different from the first embodiment as follows: the driving module 200 includes a driving unit 201, a power unit 202, and a position limiting unit 203, cooperating with each other. The tongue base 101b is able to perform curved movement to simulate the real human swallowing process. More specifically, as shown in FIG. 1, the main structure includes the swallowing module 100, the driving module 200, the adjusting module 300, and the base 400, cooperating with each other to simulate the swallowing process of food so as to realize the simulation of the food swallowing mechanism from static to dynamic. The swallowing module 100 mimics the human oral cavity which collects the swallowing food and supports the driving module 200 and it includes the bionic oral cavity assembly 101, the shred collecting assembly 102, and the supporting assembly 103. The two side plates of the maxillary base 101a of the bionic oral cavity assembly 101 connect to the mounting plates 103a of the supporting assembly 103 through L-shaped mounting plates, and the two end faces of the L-shaped mounting plates fasten to the mounting plates 103a and the maxillary base 101a by bolt or fastener. The L-shaped mounting plate is made of stainless steel or plastic and a feeding port 101a-1 is disposed on the maxillary base 101a, wherein the maxillary base 101a includes a shell and an inner wall cavity surrounded by the shell and the inner cell wall mimics the human maxillary wall. Furthermore, the shell is made of plastic, and the inner cell wall is made of soft material or rubber. The shred collecting assembly 102 is arranged on the upper partition of the mounting base 103b of the supporting assembly 103 and the shred collecting assembly 102 and the upper partition of the mounting base 103b are not fixed so as to allow cleaning up food shreds in the shred collecting assembly 102. Preferably, the shred collecting assembly 102 is made of plastic material. It should be noted that the inner wall of the maxillary base 101a is also equipped with a sensor 101a-2, wherein the sensor 101a-2 is configured to measure the pressure applied to the food in the swallowing process. Comparing to the results of the normal swallowing, the relative movement between the maxillary base 101a and the tongue base 101b can provide relative data for relevant food and medical industries. Preferably, the sensor 101a-2 is a micro force sensor or pressure sensor, etc.; and the driving module 200 embedded in the mounting chamber N1 between the upper partition and lower partition of the mounting base 103b is a power mechanism to achieve the human swallowing simulation; the adjusting module 300 positioned under the mounting base 103b can simulate the food swallowing process with multi angle and enhance the practical performance of the present invention. Furthermore, the adjusting module 300 includes a bearing assembly 301 and adjusting assembly 302, wherein the bearing assembly 301 positioned on the adjusting assembly 302 is configured to carry the swallowing module 100 and driving module 200, and the adjusting assembly 302 is configured to perform adjusting function. The base 400 includes a protective housing 401 and a base plate 402, wherein the protective housing 401 is positioned on the base plate 402 and both of them are integral construction. The protective housing 401 is positioned on the periphery of the adjusting assembly 302. The driving module 200 includes the driving unit 201, wherein one end of a first connecting rod 201a of the driving unit 201 is connected with the support member 101b-2 through an elastic cylindrical pin, and the first connecting rod 201a is an arc structure. In addition, the driving unit 201 also includes a second connecting rod 201b and a connecting rod base 201c. Two ends of the second connecting rod 201b are respectively hinged with the other end of the first connecting rod 201a and a notch 201c-1 of the connecting rod base 201c. Furthermore, the driving unit 201 also includes a stabilizing shaft 201d and a bearing seat 201e, wherein the stabilizing shaft 201d is able to support the first connecting rod 201a. One end of the stabilizing shaft 201d passes through the first connecting rod 201a, the other end is mounting on the bearing seat 201e, and the bearing seat 201e is fastened on the mounting plate 103a. The first connecting rod 201a can rotate relatively according to the movement of the stabilizing shaft 201d. Preferably, it is provided with at least two driving unit 201 which are arranged symmetrically, that is, each first connecting rod 201a of the two driving unit are disposed symmetrically on both sides of the support member 101b-2.

Furthermore, the driving module 200 also includes the power unit 202 and the position limiting unit 203, wherein a lead screw 202a of the driving unit 202 is connected with a support side bearing seat 203b through a fixed side bearing sear 203a, and the connecting rod base 201c is positioned on the periphery of the lead screw 202a. More specifically, the lead screw 202a is connected with an internal thread hole 201c-2 of the connecting rod base 201c by screwing, and the connecting rod base 201c is embedded in a slide rail 203c of the position limiting unit 203, wherein the slide rail 203c is positioned on the bottom plate of the position limiting unit 203.

The power unit 202 further includes a motor 202b passing through a fixing plate 103b-1 of the mounting base 103b and being connected with the lead screw 202a via a coupler. Preferably, the motor 202b is connected with the fixing plate 103b-1 through a bolt to ensure stable installation of the motor 202b while adjusting the angle. Preferably, the motor 202b is a servo-actuator. It should be noted that the numbers of the driving unit 201, the power unit 202, and the position limiting unit 203 are the same (the numbers of these units as shown in the drawings are only for reference).

When in use, the food is fed from the feeding port 101a-1 into the gap between the tongue base 101b and maxillary base 101a, and then the motor 202b is turned on. The motor 202b drives the lead screw 202a through the coupler such that the rotational movement of the motor 202b can be converted into the rotational movement of the lead screw 202a, and the connecting rod base 201c connected with the lead screw 202a through screwing will be in reciprocating linear motion as required. During the movement process, the second connecting rod 201b and the first connecting rod 201a of the link will be driven to perform reciprocating curved movement. The reciprocating curved movement of the first connecting rod 201a will be transformed into the reciprocating swing of the tongue base 101b. The swinging tongue base 101b and the maxillary base 101a squeeze the food gradually and finally complete the swallowing process.

Figure 5:
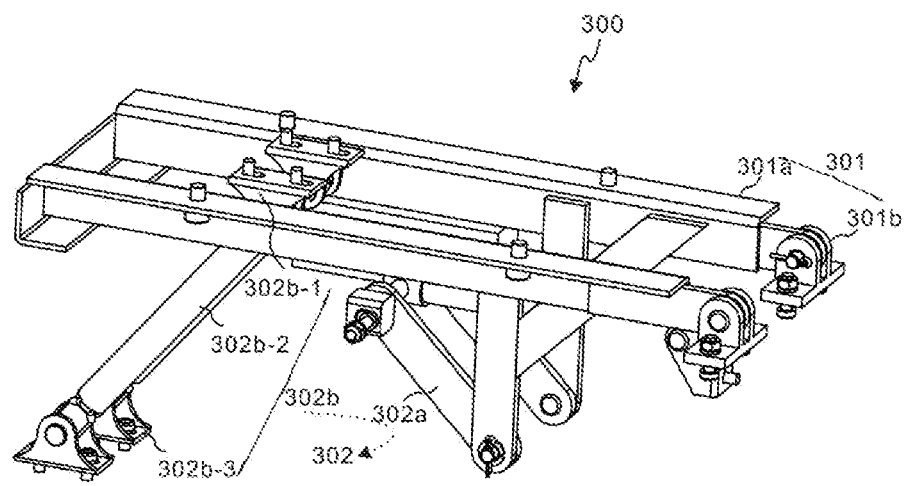
FIG. 5 is a schematic diagram of the driving module in a link motion-based food swallowing simulator according to the third embodiment of the present invention.
Figure 6:
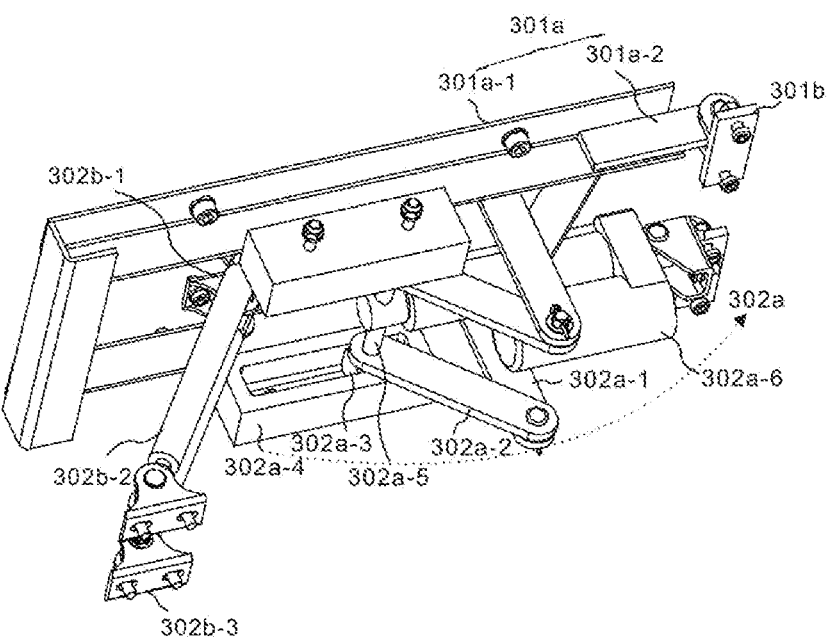
FIG. 6 is a schematic diagram of a bottom view of the driving module in the link motion-based food swallowing simulator according to the third embodiment of the present invention.

Referring to FIGS. 5 and 6, it is the third embodiment of the present invention, which is different from the above embodiments as follows: the bearing assembly 301 includes a supporting frame 301a and a rotating seat 301b, and the adjusting assembly 302 includes a primary adjusting unit 302a and an auxiliary adjusting unit 302b. More specifically, referring to FIG. 1, the main structure of the present invention includes the swallowing module 100, the driving module 200, the adjusting module 300 and the base 400. The four modules cooperate with each other to authentically simulate the swallowing process and realize the simulation of the food swallowing mechanism from static to dynamic. The swallowing module 100 mimics the human oral cavity which collects the swallowing food and supports the driving module 200 and it includes the bionic oral cavity assembly 101, the shred collecting assembly 102, and the supporting assembly 103. The two side plates of the maxillary base 101a of the bionic oral cavity assembly 101 connect to the mounting plates 103a of the supporting assembly 103 through L-shaped mounting plates, and the two end faces of the L-shaped mounting plates fasten to the mounting plates 103a and the maxillary base 101a by bolt or fastener. The L-shaped mounting plate is made of stainless steel or plastic and a feeding port 101a-1 is disposed on the maxillary base 101a, wherein the maxillary base 101a includes a shell and an inner wall cavity surrounded by the shell and the inner cell wall mimics the human maxillary wall. Furthermore, the shell is made of plastic, and the inner cell wall is made of soft material or rubber. The shred collecting assembly 102 is arranged on the upper partition of the mounting base 103b of the supporting assembly 103 and the shred collecting assembly 102 and the upper partition of the mounting base 103b are not fixed so as to allow cleaning up food shreds in the shred collecting assembly 102. Preferably, the shred collecting assembly 102 is made of plastic material. It should be noted that the inner wall of the maxillary base 101a is also equipped with a sensor 101a-2, wherein the sensor 101a-2 is configured to measure the pressure applied to the food in the swallowing process. Comparing to the results of the normal swallowing, the relative movement between the maxillary base 101a and the tongue base 101b can provide relative data for relevant food and medical industries. Preferably, the sensor 101a-2 is a micro force sensor or pressure sensor, etc.; and the driving module 200 embedded in the mounting chamber N1 between the upper partition and lower partition of the mounting base 103b is a power mechanism to achieve the human swallowing simulation; the adjusting module 300 positioned under the mounting base 103b can simulate the food swallowing process with multi angle and enhance the practical performance of the present invention. Furthermore, the adjusting module 300 includes a bearing assembly 301 and adjusting assembly 302, wherein the bearing assembly 301 positioned on the adjusting assembly 302 is configured to carry the swallowing module 100 and driving module 200, and the adjusting assembly 302 is configured to perform adjusting function. The base 400 includes a protective housing 401 and a base plate 402, wherein the protective housing 401 is positioned on the base plate 402 and both of them are integral construction. The protective housing 401 is positioned on the periphery of the adjusting assembly 302; the bearing assembly 301 includes the supporting frame 301a and the rotating seat 301b, wherein one end of an extending plate 301a-2 of the supporting frame 301a is hinged with the rotating seat 301b through a pin while the other end is fixed by welding with a frame 301a-1 of the supporting frame 301a. Preferably, the supporting frame 301a and the rotating seat 301b is made of stainless steel.

It should be noted that the adjusting assembly 302 includes the primary adjusting unit 302a and the auxiliary adjusting unit 302b, wherein a third connecting rod 302a-1 of the primary adjusting assembly 302 is connected with the frame 301a-1 of the supporting frame 301a by welding. A first fixing seat 302b-1 of the auxiliary adjusting unit 302b is connected with the lower partition of the mounting base 103b, the third connecting rod 302a-1 of the primary adjusting unit 302a is close to one end of the rotating seat 301b, and one end of the third connecting rod 302a-1 is positioned perpendicularly to the frame 301a-1. The primary adjusting unit 302a also includes a fourth connecting rod 302a-2, a slide groove 302a-4, a lever 302a-5 and a linear actuator 302a-6, wherein the third connecting rod 302a-1, the fourth connecting rod 302a-2, a sliding block 302a-3 and the slide groove 302a-4 are provided with two. The mid-position between the pushing lever of the linear actuator 302a-6 and the lever 302a-5 is connected through a sleeve, while the linear actuator 302a-6 is fastened to the protective housing 401 of the base 400 through a bolt. Each of two ends of the lever 302a-5 is configured with sliding block 302a-3, and the sliding block 302a-3 is embedded in the slide groove 302a-4. The slide groove 302a-4 is installed in the inner wall of the protective housing 401, and the two ends of the fourth connecting rod 302a-2 are respectively connected with the lever 302a-5 and the third connecting rod 302a-1. More specifically, one end of the fourth connecting rod 302a-2 is hinged with the other end of the third connecting rod 302a-1. The other end is sleeved on the periphery of the lever 302-5, and the lever 302a-5 can rotate in the connection hole of the fourth connecting rod 302a-2.

The auxiliary adjusting unit 302b further includes a gas spring 302b-2 and a second fixing seat 302b-3, wherein the two ends of the gas spring 302b-2 are respectively connected with the first fixing seat 302b-1 and the second fixing seat 302b-3, and the second fixing seat 302b-3 is fastened on the base plate 402 by screwing.

While adjusting the inclination angle, the linear actuator 302a-6 push the lever 302a-5 to move, and the lever 302a-5 drives the sliding block 302a-3 to slide in the slide groove 302a-4. Meanwhile, the lever 302a-5 pulls the fourth connecting rod 302a-2 and the fourth connecting rod 302a-2 pulls the third connecting rod 302a-1 so that the supporting frame 301a welded with the third connecting rod 302a-1 lifts slowly, forming an elevation angle. The sliding block 302a-3 and the slide groove 302a-4 is configured to limit the lever to linear movement, and to support the lever. With the lifting up of the supporting frame 301a, the gas spring 302b-2 will apply a certain force to the lower partition of the mounting base 103b so as to reduce the load of the third connecting rod 302a-1. During the swallowing simulation, food is fed from the feeding port 101a-1 into the gap between the tongue base 101b and maxillary base 101a, and then the motor 202b is turned on. The motor 202b drives the lead screw 202a through a coupler such that the rotational movement of the motor 202b can be converted into the rotational movement of the lead screw 202a, and the connecting rod base 201c connected with the lead screw 202a through screwing will be in reciprocating linear motion as required. During the movement process, the second connecting rod 201b and the first connecting rod 201a will be driven to perform reciprocating curved movement. The reciprocating curved movement of the first connecting rod 201a will be transformed into the reciprocating swing of the tongue base 101b. The swinging tongue base 101b and the maxillary base 101a squeeze the food gradually and finally complete the swallowing process. The pressure values generated during the swallowing process are measured by the sensor 101a-2. In order to prevent the side leakage, the first collection box 102a is positioned under the tongue base 101b.

It is important to note that the construction and arrangement of the present application shown in the various exemplary embodiments are merely exemplary. Although only a few embodiments are described in detail in this disclosure, those who refer to this disclosure will readily understand that many modifications can be made without substantially departing from the novel teachings and advantages of the subject matter described in this application. It is possible to make various modifications (for example, the size, scale, structure, shape, and proportion of various elements, as well as parameter values (for example, temperature, pressure, etc.), installation arrangement, use of materials, changes in color, orientation, etc.). For example, an element shown as being integrally formed may be composed of multiple parts or elements, the position of the element may be inverted or otherwise changed, and the nature or number or position of discrete elements may be altered or changed. Therefore, all such modifications are intended to be included within the scope of this invention. The order or sequence of any process or method steps may be changed or reordered according to alternative embodiments. In the claims, any "functional features" limitation is intended to cover a structure described herein that performs the described function, and is not only structurally equivalent but also equivalent structure. Other substitutions, modifications, changes, and omissions may be made in the design, operating conditions, and arrangement of the exemplary embodiments without departing from the scope of the present invention. Accordingly, the invention is not limited to a particular embodiment, but is extended to various modifications that still fall within the scope of the appended claims.

Furthermore, in order to provide a concise description of an exemplary embodiment, all features of an actual embodiment may not be described (i.e., those features that are not relevant to the best mode of carrying out the invention currently considered, or those that are not relevant to implement the invention) feature).

It should be understood that during the development of any actual implementation, such as in any engineering or design project, a large number of specific implementation decisions may be made. Such a development effort may be complex and time-consuming, but for those of ordinary skill who would benefit from this disclosure, it does not require much experimentation, and the development effort will be a routine job of design, manufacturing, and production.

It should be noted that the above embodiments are only used to illustrate the technical solution of the present invention and are not limiting. Although the present invention has been described in detail with reference to the preferred embodiments, those skilled in the art should understand that the technical solution of the present invention can be carried out. Modifications or equivalent substitutions without departing from the spirit and scope of the technical solutions of the present invention should all be covered by the claims of the present invention.

The invention claimed is:

1. A link motion-based food swallowing simulator, comprising:
    a swallowing module including a bionic oral cavity assembly (101), a shred collecting assembly (102), and a supporting assembly (103), wherein two side plates of a maxillary base (101*a*) of the bionic oral cavity assembly (101) connect to a mounting plate (103*a*) of the supporting assembly (103), wherein the shred collecting assembly (102) is positioned on a mounting base (103*b*) of the supporting assembly (103);
    a driving module (200), positioned in a mounting chamber (N1) of the mounting base (103*b*);
    an adjusting module (300), positioned under the mounting base (103*b*), including a bearing assembly (301) and an adjusting assembly (302), wherein the bearing assembly (301) is disposed on the adjusting assembly (302); and
    a base (400), including a protective housing (401) and a base plate (402), wherein the protective housing (401) is positioned on the base plate (402), and the protective housing (401) is positioned on a periphery of the adjusting assembly (302).

2. The link motion-based food swallowing simulator of claim 1, wherein the bionic oral cavity assembly (101) further comprises a tongue base (101*b*), wherein the tongue base (101*b*) is positioned on an inner side of the maxillary base (101*a*).

3. The link motion-based food swallowing simulator of claim 1, wherein an inner side of the maxillary base (101*a*) is equipped with a sensor (101*a*-2).

4. The link motion-based food swallowing simulator of claim 3, wherein the tongue base includes a tongue-shaped soft pad (101*b*-1) and a support member (101*b*-2), wherein the tongue-shaped soft pad (101*b*-1) is mounted on the support member (101*b*-2).

5. The link motion-based food swallowing simulator of claim 4, wherein the shred collecting assembly (102) includes a first collection box (102*a*), a second collection box (102*b*), a bottom slide (102*c*), and a guiding slit (102*d*), and wherein the first collection box (102*a*) is positioned at one end of a tongue tip of the tongue-shaped soft pad (101*b*-1), the bottom slide (102*c*) is positioned between the second collection box (102*b*) and a base of the tongue-shaped soft pad (101*b*-1), and the guiding slit (102*d*) is positioned at two sides of the tongue base (101*b*).

6. The link motion-based food swallowing simulator of claim 4, wherein the driving module (200) includes a driving unit (201), and one end of a first connecting rod (201*a*) of the driving unit (201) is connected with a support member (101*b*-2);
    wherein the driving unit (201) further comprises a second connecting rod (201*b*) and a connecting rod base (201*c*), and two ends of the second connecting rod (201*b*) are respectively hinged with the other end of the first connecting rod (201*a*) and a notch (201*c*-1) of the connecting rod base (201*c*).

7. The link motion-based food swallowing simulator of claim 6, wherein the driving unit (201) further comprises a stabilizing shaft (201*d*) and a bearing seat (201*e*), one end of the stabilizing shaft (201*d*) passes through the first connecting rod (201*a*), and the other end is mounted on the bearing seat (201*e*), wherein the bearing seat (201*e*) is fastened on the mounting plate (103*a*).

8. The link motion-based food swallowing simulator of claim 7, wherein the driving module (200) further comprises a power unit (202) and a position limiting unit (203), wherein a lead screw (202*a*) of the driving unit (202) is connected with a support side bearing seat (203*b*) through a fixed side bearing sear (203*a*) of the position limiting unit (203), and the lead screw (202*a*) is connected with an internal thread hole (201*c*-2) of a connecting rod base (201*c*) by screwing;
    wherein the power unit (202) further comprises a motor (202*b*), and the motor (202*b*) passes through a fixing plate (103*b*-1) of the mounting base (103*b*) and is connected with the lead screw (202*a*) via a coupler.

9. The link motion-based food swallowing simulator of claim 8, wherein the bearing assembly (301) includes a supporting frame (301*a*) and a rotating seat (301*b*), wherein one end of the supporting frame (301*a*) is hinged with the rotating seat (301*b*).

10. The link motion-based food swallowing simulator of claim 9, wherein the adjusting assembly (302) includes a primary adjusting unit (302*a*) and an auxiliary adjusting unit (302*b*), wherein a third connecting rod (302*a*-1) of the primary adjusting assembly (302) is connected with a frame (301*a*-1) of a supporting frame (301*a*), and wherein a first fixing seat (302*b*-1) of the auxiliary adjusting unit (302*b*) is connected with a lower partition of the mounting base (103*b*);
    wherein the primary adjusting unit (302*a*) further comprises a fourth connecting rod (302*a*-2), a slide groove (302*a*-4), a lever (302*a*-5) and a linear actuator (302*a*-6), wherein a push lever of the linear actuator (302*a*-6) is connected with the lever (302*a*-5), and the linear actuator (302*a*-6) is fastened to the protective housing (401) of the base (400) through a bolt, wherein a sliding block (302*a*-3) is positioned in two ends of the lever (302*a*-5), and the sliding block (302*a*-3) is embedded in a slide groove (302*a*-4), wherein two ends of the fourth connecting rod (302*a*-2) are respectively connected with the lever (302*a*-5) and the third connecting rod (302*a*-1);
    wherein the auxiliary adjusting unit (302*b*) further comprises a gas spring (302*b*-2) and a second fixing seat (302*b*-3), wherein two ends of the gas spring (302*b*-2) are respectively connected with the first fixing seat (302*b*-1) and the second fixing seat (302*b*-3).

* * * * *